United States Patent [19]
Pedersen et al.

[11] 4,143,056
[45] Mar. 6, 1979

[54] MALEIC ANHYDRIDE PRODUCTION USING THALLIUM-VANADIUM MODIFIED PHOSPHOTUNGSTIC CATALYSTS

[75] Inventors: S. Erik Pedersen, Havertown, Pa.; Ming N. Sheng, Cherry Hill, N.J.

[73] Assignee: Atlantic Richfield Company, Los Angeles, Calif.

[21] Appl. No.: 853,970

[22] Filed: Nov. 21, 1977

[51] Int. Cl.$^2$ .......................................... C07D 307/60
[52] U.S. Cl. ............................... 260/346.75; 252/437
[58] Field of Search .................................... 260/346.75

[56] References Cited
U.S. PATENT DOCUMENTS
4,003,920  1/1977  Ueeda .............................. 260/346.75

OTHER PUBLICATIONS
Ai, J. of Catalysis 49, p. 313-319 (1977).

*Primary Examiner*—Natalie Trousof
*Assistant Examiner*—Bernard Dentz
*Attorney, Agent, or Firm*—John R. Ewbank

[57] ABSTRACT

A lower unsaturated aliphatic hydrocarbon of at least 4 carbon atoms and an oxygen-containing gas react to form maleic anhydride in the presence of a catalyst having the oxides of tungsten, phosphorus, thallium, and vanadium, said catalyst being a phosphotungstic catalyst modified by minor amounts of thallium oxide and vanadium oxide, the sum of the oxides of Tl and V constituting from 1% to 15% of the catalyst, the atom ratio of Tl:V being within a range from about 2:1 to about 8:1 and the overall atomic ratios are such that W:P:Tl:V corresponds to 1:0.1–0.7:0.01–0.16:0.01–0.1. Sometimes from about 3 to about 50 volume percent steam is added to the reactant stream to enhance catalyst stability and selectivity.

3 Claims, No Drawings

1

MALEIC ANHYDRIDE PRODUCTION USING THALLIUM-VANADIUM MODIFIED PHOSPHOTUNGSTIC CATALYSTS

BACKGROUND OF THE INVENTION

1. Field of the Invention

This invention relates to the treatment of a reaction mixture of oxygen-containing gas and unsaturated normal $C_4$ hydrocarbons to form maleic anhydride over a catalyst having a novel composition and to the enhancement of the selectivity and stability of the catalyst by the control of the composition of a carrier gas component of said oxygen-containing gas.

2. Description of the Prior Art

The production of maleic anhydride by the oxidation of a hydrocarbon is complicated by the side reactins leading to the formation of carbon monoxide, carbon dioxide, and miscellaneous organic compounds. Benzene continues to be the preferred hydrocarbon feed material under appropriate feedstock price conditions. At times when the price of benzene is relatively high, compared to the price for reasonably pure normal unsaturated $C_4$ hydrocarbons, there can be economic advantages in the production of maleic anhydride from unsaturated normal $C_4$ hydrocarbons even when the yields are less than sometimes attained with benzene. Mixtures containing butadiene, butene -1, cisbutene -2, trans-butene -2, as well as mixtures containing unsaturated $C_5$ hydrocarbons comprising cyclopentadiene, pentenes, and pentadienes can be used instead of unsaturated $C_4$ hydrocarbons. MA (i.e. maleic anhydride) has been catalytically prepared by oxidation of normal butane at temperatures higher than those employed for conversion of unsaturates and at generally lower selectivities. The production of MA from butane can be deemed to be as different from making MA from unsaturated normal $C_4$ hydrocarbons as is the making of MA from benzene.

A considerable variety of catalysts have been found to have some activity for the oxidation of normal butenes to MA. However, the relative proportions of carbon dioxide, carbon monoxide, and undesired organic impurities resulting from the use of any of the many previously proposed catalysts has been high enough to jeopardize the profitability of MA production. A high proportion of the literature descriptions of catalysts for production of MA concern catalysts which were sufficiently unsatisfactory that they are conveniently designated as abandoned scholarly investigations.

In the production of MA from n-butenes, there has been a long term preference for catalysts featuring vanadium oxide, as exemplified by Kerr in U.S. Pat. No. 3,156,705. Multiple metal catalysts have been proposed by Milberger et al in U.S. Pat. No. 3,907,834, and Otaki et al in U.S. Pat. No. 3,992,419. However, these catalysts have not provided yields which could be satisfactory commercially under current engineering standards. In a series of Ueeda patents including U.S. Pat. Nos. 3,906,008, 3,975,407, and 4,003,920, all the disclosures of which are deemed here reiterated, 1-butene is oxidized to MA over a catalyst featuring the oxides of tungsten and phosphorus and modified by an appropriately selected metal oxide promoter. Some persistent, proficient attempts to reproduce the reported selectivities, yields and conversions of selected examples of said Ueeda patents have been unsuccessful. Furthermore, relatively poor yields for preparing MA from n-butenes have been reported by M. Ai in two articles entitled "The Activity of $WO_3$ Based Mixed Oxide Catalysts", J. of Catalysis 49, 305–312 and 49, 313–319 (1977), concerning modified phosphotungstic catalysts of the Ueeda type. As explained by Ueeda in U.S. Pat. No. 3,906,008, and further illustrated in comparative example 2 of U.S. Pat. No. 4,003,920, the presence of vanadium in their phosphotungstic type of catalyst led to unsatisfactory yields of M.A.

Notwithstanding the persistent effort at improving catalyst, the chemical industry has continued to seek a catalyst having acceptable stability, conversion and selectivity for producing maleic anhydride from unsaturated aliphatic hydrocarbons.

SUMMARY OF THE INVENTION

In accordance with the present invention, maleic anhydride is prepared by the oxidation of an unsaturated aliphatic hydrocarbon having at least 4 carbon atoms in the presence of a phosphotungstic catalyst modified by the presence of from 1 to 15% of oxides of thallium and vanadium, the unit atom ratio of thallium to vanadium being within the range from 2 to 8, and the overall atom ratios being such that W:P:Tl:V corresponds generally to 1:0.1–0.7:0.01–0.16:0.01–0.1, the formulation of a series of catalysts for experimental program being expressed more conveniently by atom ratios than by some of the alternative equivalent expressions of composition.

The present invention concerns a novel four component catalyst featuring oxides of tungsten and phosphorus modified by small amounts of oxides of thallium and vanadium. This type of catalyst gives yields of MA which have attractiveness under contemporary engineering standards and shows stability and indicated life which satisfy contemporary engineering standards. This catalyst is distinctly different from the Ueeda type. By the present invention, an outstanding catalyst can be prepared by combining carefully selected proportions of oxides of vanadium with thallium in a catalyst having carefully selected proportions of oxides of tungsten and phosphorus, thus differing significantly from the teaching of the Ueeda patents that vanadium oxide is an unsatisfactory component of a phosphotungstic catalyst for M.A. production.

Desirably, steam constitutes from about 3% to about 50% of the volume of the reactant stream.

The nature of the invention is further clarified by reference to a plurality of examples.

EXAMPLES 1–7

Tungstic oxide can be prepared by the dehydration of any of several related compositions such as ammonium tungstate, tungstic acid, ammonium metatungstate, or the like. If the calcination is conducted at an excessive temperature, then the desirable catalytic properties are not achieved. Prior literature suggests that the conversion from a material such as ammoniumtungstate to tungstic oxide should be conducted at about 800° C. In the development of the present invention, it was established that better catalysts are obtained by preparing the tungstic oxide at a temperature of about 300° C.

An aqueous dispersion is prepared consisting of water and the desired precursors for the catalyst. There are added to the water the tungstic oxide powder and aqueous phosphoric acid and appropriate compounds for introducing thallium and vanadium. The atom ratio of thallium to vanadium must be from about 2 to 1 to about 8 to 1. Certain preferred catalysts employ such an atom ratio of about 4 to 1. That is, the atom percent of vanadium must be from 12 to 50% of the atom percent of thallium, and desirably is about 25%. In laboratory preparations, it is convenient to use thallous chloride to supply the thallium oxide, inasmuch as substantially all of the chloride is volatilized during catalyst preparation prior to the butene oxidation step. Thus the catalyst is accurately designated as a plural metal oxide phosphate catalyst notwithstanding such use of thallous chloride in the preparation thereof. Inasmuch as the calcined catalyst is essentially a mixed oxide catalyst and inasmuch as the trace amounts of acetate, sulfate, chloride, bromide, and/or nitrate which might conceivably remain as residues after calcination of the catalyst are not significantly poisonous to the catalyst, it is possible to use compounds such as thallous acetate, thallium nitrate, thallium carbonate, thallous hydroxide, thallous oxalate, or thallous phosphate in catalyst preparation. The vanadium desirably is introduced as vanadic acid, as an oxide of vanadium, or as a conventional precursor compound for catalytic vanadium oxide, but the introduction of acetate, halide, or related residue with the vanadium does not destroy the operativeness of the catalyst.

A dispersion of 500 ml of catalyst precursors was prepared by mixing water with 360 grams of tungsten trioxide, 56.0 grams of 85% phosphoric acid, 23.7 grams of thallous chloride, and 4.4 grams of vanadium pentoxide. The bulk of the water was removed by heating to prepare a homogeneous paste which was thereafter dried to a solid in an oven maintained at 120° C. The dried solids were pulverized and activted by heating in air at 500° C for 2 hours. The activated powder was subjected to mechanical pressure to form pellets and the pellets were crushed and sieved to retain particles in the 8–14 mesh size.

The catalyst was analyzed and it was established that the atomic ratio or W:P:Tl was 1:0.31:0.064:0.016. Thus the atom percent of vanadium was 25% of the atom percent of thallium, or the thallium to vanadium atom ratio was 4 to 1.

Laboratory apparatus for the preparation of maleic anhydride employed a heat transfer system featuring a fluidized sand bath for maintaining a heated zone uniformly at a steady temperature. A stainless steel tube having an inside diameter of about ⅝ inch was shaped as a U-tube to serve as the reactor. The lower half of the U-tube portion of the reactor was filled with catalyst granules (8–14 mesh size) and the reactant stream was sent downwardly through the catalyst zone to an effluent zone.

The gaseous effluent from the reactor was subjected to automatically recording measurements by I.R. and gas chromatography for determining the concentration in the effluent stream of carbon dioxide, carbon monoxide, maleic anhydride and hydrocarbon. The reactant stream flowed through a series of water traps adapted to absorb all of the maleic anhydride and/or other normally solid and/or normally liquid compounds of the reactant stream. The maleic anhydride reacted with the aqueous solution in the traps to form maleic acid. The aqueous solution containing the maleic acid was analyzed for minor by-products.

In each preparation of maleic anhydride in Examples 1 – 7, the volume of catalyst was 50 ml, the reactant stream consisted of air containing 1% by volume 1-butene, at an apparent contact time of 2.4 seconds. The mass balance was calculated for each preparation and only runs in which such data confirmed the significant reliability of the analyses are reported. In those preparations featuring injection of steam, the initial measurement of steam injection rate was on the basis of volume percent of feed.

Data relating to the preparation of maleic anhydride are shown in Table 1.

Table 1

MA Using W-P-Tl-V Catalyst 1:0.31:0.064:0.016

| Ex | Temp. °C | $H_2O$ % in feed | Conv. (%) | Selectivity MA (%) | Yield MA (%) | CO (%) | $CO_2$ (%) | Acetic Acid (%) | Acrylic Acid (%) |
|---|---|---|---|---|---|---|---|---|---|
| 1 | 410 | 0 | 90 | 58.4 | 52.6 | 19.9 | 16.1 | 1.7 | 3.5 |
| 2 | 430 | 0 | 97 | 58.9 | 57.1 | 20.1 | 16.3 | 1.0 | 2.6 |
| 3 | 445 | 0 | 100 | 60.6 | 60.6 | 18.5 | 15.0 | 1.2 | 2.6 |
| 4 | 460 | 0 | 100 | 61.5 | 61.5 | 19.5 | 14.4 | 0.6 | 2.4 |
| 5 | 445 | 10 | 90 | 63.3 | 57.0 | 17.4 | 14.0 | 2.4 | 3.4 |
| 6 | 460 | 10 | 98 | 62.4 | 61.2 | 19.4 | 12.9 | 2.1 | 3.2 |
| 7 | 460 | 5 | 93 | 63.4 | 59.0 | 18.9 | 12.7 | 2.5 | 2.4 |

The inclusion of the steam in the reactant stream slightly curtailed the conversion but enhanced the selectivity for catalysts of Examples 5, 6 and 7 at the conditions employed in Table 1.

EXAMPLES 8 – 21

Maleic anhydride was prepared using approaches generally the same as in Examples 1 – 8, but varying the Tl/V unit atom ratio from 2 to 6. The presence of steam in the feedstream proved to be beneficial, especially when steam concentration in the reactant stream entering the catalytic zone contained from about 3% to about 50% steam. The apparent contact time can be varied throughout a range from about 1 to about 5 seconds.

Data relating to the preparation of MA (maleic anhydride) are shown in Table 2.

Table 2

MA Using Modified Phosphotungstic Catalyst

| Code | Catalyst W:P:Tl:V 1:0.238:Q:Y Q Tl | Y V | Tl/V | Contact sec | Temp. °C | g/hr. $H_2O$ addn. | Conv. % | MA Select mol % | Yield MA mol % | CO mol % | $CO_2$ mol % | Acetic Acid % | Acrylic Acid % |
|---|---|---|---|---|---|---|---|---|---|---|---|---|---|
| Ex 8 | 0.092 | 0.023 | 4 | 2.4 | 445 | 0 | 98 | 59.6 | 58.4 | 21.1 | 14.0 | 0.8 | 1.2 |
| Ex 9 | 0.092 | 0.023 | 4 | 2.4 | 460 | 0 | 100 | 59.0 | 59.0 | 22.4 | 12.9 | 0.8 | 1.3 |
| Ex 10 | 0.092 | 0.023 | 4 | 2.8 | 460 | 10 | 100 | 62.8 | 62.8 | 20.2 | 12.3 | 1.7 | 2.3 |
| Ex 11 | 0.060 | 0.03 | 2 | 2.4 | 445 | 0 | 100 | 55.6 | 55.6 | 24.8 | 15.1 | 0.5 | 2.4 |
| Ex 12 | 0.060 | 0.03 | 2 | 2.4 | 445 | 10 | 97 | 59.1 | 57.3 | 21.2 | 14.2 | 1.2 | 3.5 |

Table 2-continued

MA Using Modified Phosphotungstic Catalyst

| Code | Catalyst W:P:Tl:V 1:0.238:Q:Y Q Tl | Y V | Tl/V | Contact sec | Temp. °C | g/hr. H$_2$O addn. | Conv. % | MA Select mol % | Yield MA mol % | CO mol % | CO$_2$ mol % | Acetic Acid % | Acrylic Acid % |
|---|---|---|---|---|---|---|---|---|---|---|---|---|---|
| Ex 12 | 0.060 | 0.03 | 2 | 2.4 | 460 | 10 | 100 | 59.3 | 59.3 | 22.5 | 13.6 | 1.5 | 3.0 |
| Ex 14a | 0.032 | 0.016 | 2 | 2.4 | 460 | 0 | 100 | 59.1 | 59.1 | 21.0 | 14.3 | 0.4 | 1.0 |
| Ex 14f (70 hrs.) | 0.032 | 0.016 | 2 | 2.4 | 460 | 0 | 1009 | 55.9 | 55.9 | 23.6 | 16.1 | 0.4 | 0.9 |
| Ex 15 | 0.093 | 0.031 | 3 | 2.4 | 445 | 0 | 100 | 58.3 | 58.3 | 21.5 | 15.4 | 0.9 | 2.5 |
| Ex 16 | 0.093 | 0.031 | 3 | 2.4 | 445 | 10 | 90 | 63.1 | 56.8 | 18.3 | 12.5 | 2.8 | 2.2 |
| Ex 17 | 0.093 | 0.031 | 3 | 2.4 | 460 | 10 | 95 | 62.3 | 59.2 | 18.5 | 12.6 | 22.4 | 2.6 |
| Ex 18 | 0.15 | 0.031 | 5 | 2.4 | 445 | 0 | 84 | 63.4 | 53.3 | 22.0 | 10.8 | 0.5 | 1.5 |
| Ex 19 | 0.15 | 0.031 | 5 | 2.5 | 460 | 0 | 85 | 62.0 | 52.7 | 20.8 | 12.2 | 0.7 | 1.3 |
| Ex 20 | 0.15 | 0.031 | 5 | 2.8 | 460 | 10 | 83 | 63.1 | 52.4 | 21.6 | 12.0 | 1.3 | 1.5 |
| Ex 21a | 0.090 | 0.015 | 6 | 3.0 | 460 | 10 | 90 | 61.5 | 55.4 | 18.9 | 14.9 | 2.0 | 2.3 |
| Ex 21f (250 hrs.) | 0.090 | 0.015 | 6 | 3.0 | 460 | 10 | 91 | 60.3 | 54.9 | 19.2 | 15.1 | 2.2 | 3.0 |

Attention is directed to the fact that the unit atom ratio of thallium to vanadium appears to be a more significant factor than some of the other variables which might be investigated.

The correlation between amount of thallium and MA selectivity are as follows:

| Atom Fraction Tl | Yield MA % | Selectivity MA % | Example |
|---|---|---|---|
| 0.032 | 59.1 | 59.1 | 14a |
| 0.064 | 59.0 | 63.4 | 7 |
| 0.064 | 59.3 | 59.3 | 13 |
| 0.092 | 62.8 | 62.8 | 10 |
| 0.093 | 56.8 | 63.1 | 16 |
| 0.092 | 55.4 | 61.5 | 21a |
| 0.150 | 52.4 | 63.1 | 20 |

A review of such data provided little guidance concerning plans for future catalysts.

The correlation between the amount of vanadium and MA selectivity are as follows:

| Atom Fraction | Yield MA % | Selectivity MA % | Example |
|---|---|---|---|
| 0.016 | 59.0 | 63.4 | 7 |
| 0.016 | 59.1 | 59.1 | 14a |
| 0.023 | 62.8 | 62.8 | 10 |
| 0.031 | 59.3 | 59.3 | 13 |
| 0.031 | 59.2 | 62.3 | 17 |
| 0.031 | 52.4 | 63.1 | 20 |

A review of the vanadium data provided little guidance concerning attractive potentialities for future research.

The correlation between the total amount of modifier in the phosphotungstic catalyst and MA selectivity are as follows:

| Tl Plus V | Yield MA % | Selectivity MA % | Example |
|---|---|---|---|
| 0.048 | 59.1 | 59.1 | 14a |
| 0.080 | 59.0 | 63.4 | 7 |
| 0.090 | 59.3 | 59.3 | 13 |
| 0.105 | 55.4 | 61.5 | 21a |
| 0.115 | 62.8 | 62.8 | 10 |
| 0.124 | 59.2 | 62.3 | 17 |
| 0.181 | 52.4 | 63.1 | 20 |

No reliable trend was recognized during a review of such data.

Surprisingly, however, the review of either selectivity data or yield data suggested advantages for control of the unit atom ratio of thallium to vanadium. Advantageous results, compared to prior art teachings, are attainable throughout a unit ratio from 2 to about 8. Surprisingly better results are indicated for a unit ratio of the general range of 3 to 4.

A correlation of unit atom ration of thallium to vanadium to data concerning selectivity and yield are as follows:

| Tl/V | Yield MA % | Selectivity MA % | Example |
|---|---|---|---|
| 2 | 59.3 | 59.3 | 13 |
| 3 | 59.2 | 62.3 | 17 |
| 4 | 61.2 | 62.4 | 6 |
| 4 | 62.8 | 62.8 | 10 |
| 5 | 52.4 | 63.1 | 20 |
| 6 | 55.4 | 61.5 | 2a |

Such data indicate that the ratio of thallium to vanadium atom ratio is preferably about 3.5 to about 4.5, desirably about 4.

Exact comparisons amongst examples (and/or the larger number of preparations of MA deemed redundant and not reported herein) are not feasible because of variations in temperature, space rate, stability, steam content, etc., but the tabulated data provide useful guidance in recognizing significant factors affecting catalyst composition.

CONTROL PREPARATIONS A - B

Several literature references have shown data establishing that a phosphotungstate catalyst containing a minor amount of vanadium is commercially unsatisfactory and inferior to many other activated phosphotungstate catalysts for preparing MA from butenes. The concept of a four component catalyst comprising another metal oxide and vanadium oxide was investigated, leading to the discovery that the combination of thallium and vanadium were surprisingly special, achieving outstanding selectivity, stability and activity. Selected examples of less satisfactory catalysts help to illustrate the point that a fourth component with vanadium does not assure satisfactory performance.

A catalyst was prepared in which antimony cooperated with vanadium, the ratios of W:P:Sb:V being 1:0.31:0.03:0.03. Using the apparatus and general method of Example 1, n-butenes were oxidized to MA at 100% conversion, but with a selectivity of only 39.4%. In a repetition of the preparation, the selectivity appeared to be 39.9%, so that the average was 39.7%.

Such a low selectivity would be below that of interest to commercial production of MA.

In promoting partial oxidation as distinguished from complete combustion of organic materials, silver has a remarkable achievement record, both as a significant and as promoter component of a catalyst. However, a silver-promoted vanadium phosphotungstate catalyst proved to have objectionably low selectivity when tested for MA preparation by a method generally (except for catalyst composition) following Example 1. In duplicate runs at 460° C, the selectivity was 28.5% and 30.7%, averaging 29.6%. By lowering the temperature to 445° C, the selectivity was raised to 32.2%, still too low to arouse commercial interest.

By the present invention, the vanadium promotes the phosphotungstate catalyst when combined with an atom concentration of thallium which is from 2 8 times the atom concentration of vanadium, and it is this unexpected and unobvious discovery for which patent protection is sought.

The invention claimed is:

1. In the method for the production of an effluent stream containing maleic anhydride, said method using a feed gas stream comprising a major amount of carrier gas, a controlled amount of oxygen, and a controlled amount of an unsaturated aliphatic normal hydrocarbon containing at least 4 carbon atoms, the proportions of oxygen and hydrocarbon providing in said feed gas stream a non-explosive mixture at reaction conditions, and said feed gas stream is converted at a temperature from 250° C to 650° C in a catalytic zone to form an effluent stream containing maleic anhydride, the improvement which consists of:

employing as the catalyst in said catalytic zone a catalyst having as active ingredients the oxides of tungsten, phosphorus, thallium and vanadium, said catalyst being a phosphotungstic catalyst modified by minor amounts of thallium oxide and vanadium oxide, the sum of the oxides of Tl and V constituting from 1% to 15% by weight of the catalyst, the atom ratio of Tl:V being within the range from about 2:1 to about 8:1, and the overall atomic ratio's are such that Tl:V correspond to 1:0.1–0.7:0.01–0.16:0.01–0.1.

2. The method of claim 1 in which the composition of the carrier gas is controlled to include from about 3 to about 50 volume percent steam.

3. The method of claim 1 in which the unsaturated aliphatic hydrocarbon is a gas stream containing a predominant volume of normal butenes.